United States Patent [19]

Andrulis, Jr. et al.

[11] Patent Number: 4,565,884
[45] Date of Patent: Jan. 21, 1986

[54] BIS-PLATINUM COMPLEXES AS ANTITUMOR AGENTS

[75] Inventors: Peter J. Andrulis, Jr., Washington, D.C.; Paul Schwartz, Rockville, Md.

[73] Assignee: Andrulis Research Corporation, Bethesda, Md.

[21] Appl. No.: 608,743

[22] Filed: May 10, 1984

Related U.S. Application Data

[63] Continuation-in-part of Ser. No. 493,177, May 10, 1983, abandoned.

[51] Int. Cl.⁴ ............................................. C07F 15/00
[52] U.S. Cl. .................... 556/137; 534/661; 534/662; 534/683; 534/684; 536/121; 544/301; 556/19; 548/106; 514/492; 534/722; 534/841
[58] Field of Search .................. 260/429 R; 424/287; 260/146 D, 148, 149, 150; 548/106; 544/301; 536/121

[56] References Cited

U.S. PATENT DOCUMENTS

| | | | |
|---|---|---|---|
| 4,115,418 | 9/1978 | Gale et al. | 260/429 R |
| 4,119,653 | 10/1978 | Tobe et al. | 260/429 R |
| 4,137,248 | 1/1979 | Gale et al. | 260/429 R |
| 4,169,846 | 10/1979 | Kidani et al. | 260/429 R |
| 4,200,583 | 4/1980 | Kidani et al. | 260/429 R |
| 4,225,529 | 9/1980 | Hydes et al. | 260/429 R |
| 4,230,631 | 10/1980 | Hydes et al. | 260/429 R |
| 4,250,189 | 2/1981 | Hydes et al. | 260/429 R X |
| 4,255,347 | 3/1981 | Kidani et al. | 260/429 R |
| 4,256,652 | 3/1981 | Kidani et al. | 260/429 R |
| 4,271,085 | 6/1981 | Amundsen et al. | 260/429 R |
| 4,283,342 | 8/1981 | Yolles | 260/345.1 |
| 4,322,362 | 3/1982 | Kaplan et al. | 260/429 R |
| 4,359,425 | 11/1982 | Totani et al. | 260/429 R |
| 4,410,544 | 10/1983 | Berg et al. | 260/429 R X |
| 4,452,812 | 6/1984 | Macquet | 260/429 R X |

OTHER PUBLICATIONS

Rochon et al, J. of Clinical Hematology and Oncology, vol. 12, No. 2, pp. 39–43 (1982).

Primary Examiner—Helen M. S. Sneed
Attorney, Agent, or Firm—Millen & White

[57] ABSTRACT

Bis-platinum complexes having the formula

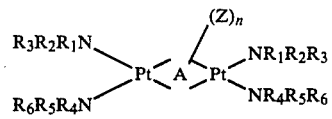

wherein A is a ligand having two pairs of platinum-coordinating acidic groups which are each independently a carboxylate, phenolate, sulfonate or phosphonate group, each said pair being capable of coordinating with a platinum ion to form a 5–10 membered chelate ring; Z is a water-solubilizing group; n is 0 or a positive integer, with the proviso that n is 0 only when at least one of said platinum-coordinating acidic groups is sulfonate or phosphonate or when at least one platinum ion is a Pt(IV) ion; and $R_1$, $R_2$, $R_3$, $R_4$, $R_5$ and $R_6$ are each independently H or a $C_{1-20}$ alkyl, aryl, aralkyl, or alkaryl group, or together form one or more $C_{1-30}$ alkylene, cycloalkylene, arylene, aralkylene or alkarylene groups; or a pharmaceutically acceptable salt thereof, are useful as readily water-soluble antitumor agents.

20 Claims, No Drawings

BIS-PLATINUM COMPLEXES AS ANTITUMOR AGENTS

This application is a continuation-in-part of applicants' copending U.S. patent application Ser. No. 493,177, entitled "BIS-PLATINUM COMPLEXS AS ANTITUMOR AGENTS", filed May 10, 1983 now abandoned.

BACKGROUND OF THE INVENTION

This invention relates to bis-platinum complexes and their use as antitumor agents in humans and animals.

It is known that Cisplatin, cis-[Pt(NH$_3$)$_2$Cl$_2$] is effective against several types of animal tumors and has been used successfully in treating certain types of malignancies in humans. A number of other platinum complexes have been tested for antitumor activity, e.g., increased life span for mice having implanted tumors such as L-1210 lymphoid leukemia.

An oligomeric platinum complex is disclosed in U.S. Pat. No. 4,128,342 to Yolles. These complexes contain bridging halogen ligands as well as a number of platinum ions in both therapeutic and non-therapeutic forms in the complex.

Three bis-platinum complexes were reported by Rochon et al., J. Clin. Hematology & Oncology, 12, 39–43 (May, 1982). Two of those showed no activity against L-1210 lymphoid leukemia, while a third showed a low level of activity but also showed significant toxicity.

Gale et al., U.S. Pat. 4,137,248, and Kidani et al., U.S. Pat. No. 4,169,846, disclose monomeric complexes of [1,2-diaminocyclohexane]Pt (II). The disclosures of the foregoing patents are incorporated herein by reference.

A need continues to exist for platinum complexes having appreciable water solubility to facilitate intravenous injection, along with significant antitumor activity and low toxicity.

OBJECTS OF THE INVENTION

One object of the present invention is to provide platinum antitumor agents having appreciable water solubility, significant antitumor activity and relatively low toxicity.

Another object of the invention is to provide platinum antitumor agents having a high yield of therapeutic platinum in a form which is advantageous for intravenous administration.

A further object of this invention is to provide a method of tumor therapy which avoids disadvantages in prior art methods.

SUMMARY OF THE INVENTION

These and other objects of the invention can be achieved by a bis-platinum complex having the formula I

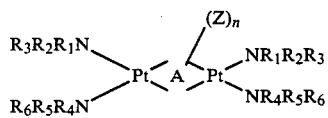

wherein A is a ligand having two pairs of platinum-oordinating acidic groups which are each independently a carboxylate, phenolate, sulfonate or phosphonate group, each said pair being capable of coordinating with a platinum ion to form a 5–10 membered chelate ring; Z is a water-solubilizing group; n is 0 or a positive integer, with the proviso that n is 0 only when at least one of said platinum-coordinating acidic groups is sulfonate or phosphonate, or when at least one platinum ion is a Pt(IV) ion; and R$_1$, R$_2$, R$_3$, R$_4$, R$_5$ and R$_6$ are each independently H or a C$_{1-20}$ alkyl, C$_{3-20}$ carbocyclic or heterocyclic aryl, aralkyl or alkaryl group, or together form one or more C$_{1-30}$ alkylene, C$_{3-20}$ carbocyclic or heterocyclic cycloalkylene, arylene, aralkylene or alkarylene groups; or a pharmaceutically acceptable salt thereof.

In a method of use aspect, the present invention provides a method for tumor therapy in humans and animals, comprising administering to a human or animal subject having a tumor an antitumor effective amount of the foregoing bis-platinum complex.

DETAILED DISCUSSION

The bis-platinum complexes of the invention each have a central ligand, A, which may also bear one or more water-solubilizing groups, Z. In general, A can be any organic group incorporating in its structure the aforementioned two pairs of platinum-coordinating acidic groups, in the proper geometry for forming two 5–10 membered chelate rings with platinum ions.

Suitable such ligands include, but are not limited to, mononuclear or polynuclear aromatic ring systems, the latter preferably dinuclear or trinuclear, each said aromatic ring being a substituted or unsubstituted carbocyclic or heterocyclic aromatic ring. More specifically, the aromatic ring system can be a benzene or naphthalene ring system, e.g.,

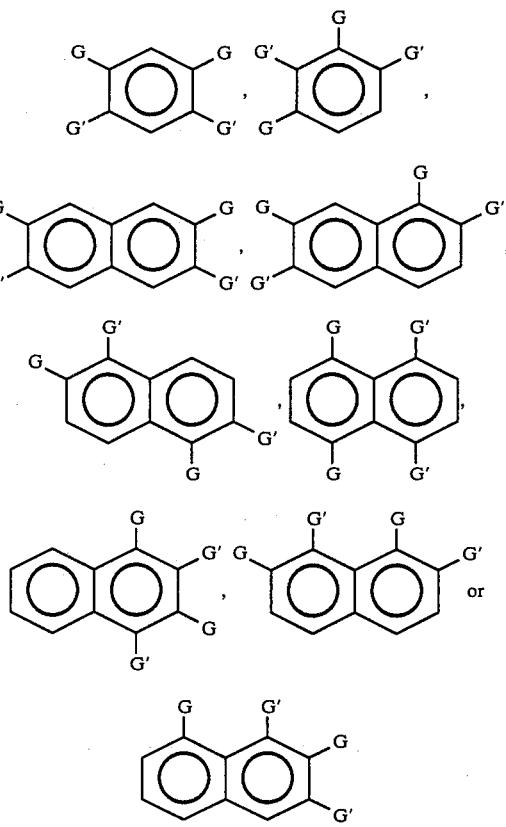

wherein G and G' are said pair of platinum-coordinating acid groups. Preferred such groups include those wherein G and G' are both carboxylate groups and those wherein at least one G or G' is a phenolate oxygen. It will also be understood that carboxylate, sulfonate and phosphonate groups need not be attached directly to the ring system, but can be separated therefrom, e.g., by short chains, preferably aliphatic lower alkylene chains, consistent with the requirement that the chelate ring to platinum be 5–10 atoms in size.

The aromatic ring systems can include heteroatoms, preferably oxygen and/or nitrogen atoms, with the nitrogen atoms preferably having unshared electron pairs which are part of the pi-electron system of the aromatic ring, so that they are of low basicity and do not tend to compete with the acidic chelating functions for coordination sites on the platinum ions. Highly nucleophilic heteroatoms, e.g., sulfur, phosphorus and the like, are preferably avoided since they will tend to bind too tightly to platinum ions. Examples of such heteroaromatic systems include, e.g., benzofuran, indole, chromene, benzopyran, indolizine and the like.

The aromatic systems need not be fused ring systems but can also be, e.g., biphenyl, terphenyl, diphenylmethane, diphenylbutane and the like, as well as mixed fused and non-fused systems, e.g., phenylnaphthalene, benzylnaphthalene, phenylbenzofuran, and the like.

Suitable ligands, A, can also include alicyclic ring systems, including mononuclear or polynuclear, substituted or unsubstituted, carbocyclic or heterocyclic alicyclic ring systems. Examples include cyclopropane, cyclobutane, cyclohexane, cycloheptane and larger rings, linked or fused to other similar rings, optionally including non-nucleophilic heteroatoms, e.g., oxygen, and preferably excluding non-aromatic nitrogen atoms and the aforementioned nucleophilic heteroatoms. Again, mixed fused and unfused ring assemblies can be used, including mixed alicyclic and aromatic ring systems, spirocyclic systems, and ring systems linked by one or more atoms in a chain, preferably an aliphatic alkylene moiety. A pair of platinum-coordinating acidic groups can both be located on the same atom on an alicyclic ring, e.g., in cyclobutane-1,1,3,3-tetracarboxylate, and like structures.

Also suitable as ligands, A, are aliphatic groups bearing appropriately located pairs of platinum-coordinating acidic groups. Examples include 2,5-dicarboxyadipate, 3,12-dicarboxytetradecanedicarboxylate and the like.

It will be understood that many other variants can be used for the central ligand, A, and all such variants are included within the scope of this invention, provided that they meet the criteria generally set forth above.

Any of the foregoing ligands may be substituted by any non-interfering substituents, e.g., alkyl, halogen, nitro, ether, ester, amide and the like, preferably containing not more than about 10 carbon atoms.

The chelate ring including each pair of platinum-coordinating acidic groups and its coordinated platinum ion, can be a 5–10 membered ring, but is preferably a 5–8 membered ring, more preferably a 6–7 membered ring. Preferably, not more than one acidic coordinating group is sulfonate or phosphonate, and in such cases, it is not necessary to provide an additional water-solubilizing group, Z, since sulfonate and phosphonate groups coordinate somewhat more loosely with platinum and are capable of dissociating relatively rapidly in water and serving as a solubilizing group. However, the presence of a water-solubilizing group, Z, is not excluded even when one or more platinum-coordinating acidic groups is sulfonate or phosphonate.

It will be understood that the two chelate rings need not be the same size, and the two pairs of platinum-coordinating acidic groups in the ligand, A, also need not be the same. In fact, it may be advantageous to have chelate rings which bind their respective platinum ions with significantly different binding constants, so that release of platinum will occur at different rates from the two chelate binding sites, thereby providing added flexibility in designing dose-response properties of potential therapeutic utility.

Examples of this type of unsymmetrical chelation can include binding of one platinum ion by a salicylate-type chelation while the other platinum ion is bound by a dicarboxylate, e.g., phthalate-type, chelation, wherein both the chelating groups and the chelate ring size are varied; catechol-type chelation provides yet a smaller chelate ring and a tighter chelate binding; dicarboxylate chelation at, e.g., the 1,8-positions of a naphthalene ring system forms an 8-membered chelate ring, which can be combined with vicinal dicarboxylate chelation in a 7-membered ring to provide variation in chelate binding properties for a single bis-platinum complex. Other examples will be readily apparent to the ordinary skilled art worker.

Water-solubilizing groups, Z, improve the solubility in water of the bis-platinum complexes of the invention. One type of water-solubilizing group is an acidic function which can be converted to its salt in alkaline solution, e.g., aqueous sodium bicarbonate. This renders the complex readily soluble in water and facilitates its dissolution in a sterile injection vehicle for intravenous infusion. The water solubility of Cisplatin is about 1 mg/ml in water. Bis-platinum complexes having equivalent potency to Cisplatin will advantageously have at least equivalent solubility.

It will be understood that significantly more potent antitumor agents can be administered in more dilute solution and the requirement for water solubility is less critical. On the other hand, relatively high solubility in water can be most advantageous for antitumor agents, since it permits administration in a concentrated solution, i.e., in a small volume of injection or infusion vehicle. This can be particularly advantageous where it is desirable to administer the antitumor agent in the vicinity of a tumor location, e.g., by intravenous or intraarterial administration over a relatively short period of time for maximum impact at the tumor site.

Preferably, the solubility of a complex according to the invention is at least about 1 m9/ml in water or dilute alkali, e.g., 1% $NaHCO_3$, more preferably at least about 10 mg/ml. For more potent complexes, a solubility of at least about 0.01 mg/ml is preferable, more preferably at least about 0.1 mg/ml in water or dilute alkali.

One useful and preferred type of water-solubilizing group is a phenolate, carboxylate, sulfonate or phosphonate group similar to the platinum-coordinating acidic groups forming the chelate rings, preferably sulfonate or carboxylate. For example, where a tetracarboxylate is used as the ligand, A, the addition of a fifth carboxylate group to the ligand provides a water-solubilizing function which permits facile dissolution of the complex in dilute aqueous bicarbonate. Where the group, Z, is an acidic function, the bis-platinum complex of the invention may be provided as a pharmaceutically acceptable salt thereof, e.g., a sodium, potassium, magnesium, or calcium salt, or the like.

Another suitable type of water-solubilizing group is a mono- or polyhydroxylic group, preferably a $C_{1-12}$ hydroxylic group. Convenient sources of such groups are derivatives of mono- or polysaccharides, e.g., ribityl, sorbityl, glucosyl and the like. These groups can be attached to the central portion of the ligand, A, by a variety of conventional reactions, including, but not limited to, condensation, alkylation, esterification, etherification and the like.

It is also possible for the water-solubilizing moiety, Z, to be incorporated directly in the ligand, A. For example, two phthalate groups can be joined to either end of a sugar derivative by means of any of the foregoing steps, whereby the water-solubilizing group, Z, links the two portions of the ligand, A, bearing the two pairs of platinum-coordinating acidic groups.

Several such water-solubilizing groups, Z, can be present on the central ligand, A. Thus, rather than a single polyhydroxylic "tail", it may be advantageous to have several shorter hydroxylic substituents on the ligand. The number of such substituents is advantageously no larger than necessary to achieve suitable water solubility for the complex and this will vary as a function of the detailed structure of the ligand, A, and of the amine substituents coordinated to the platinum ions. Where n is a positive integer, it is preferably 1-4, more preferably 1-2 and most preferably 1.

It is often the case that Pt(II) complexes will have low solubility in water unless water-solubilizing groups are present. Where at least one of the platinum ions is a Pt(IV) ion, the water solubility of the complex will generally be sufficiently high so that additional water-solubilizing groups, Z, will not generally be necessary. Where "Pt" is other than Pt(II), it will be understood to include coordinated water molecules and/or counter-ions to balance the charge of the complex. The complex may be isolated as a hydrate.

The water-solubilizing groups, Z, can include more than one type of water-solubilizing function, e.g., combinations of carboxyl, sulfonate, phosphonate, phenolate, hydroxyl, ether, ester groups and the like, on the same or different moieties, Z. Other equivalent water-solubilizing functions will be apparent to one of ordinary skill in the art, and such equivalents are included within the scope of the present invention.

The substituents on the amine groups coordinated to the platinum ions, $R_1$–$R_6$, can each independently be hydrogen atoms, $C_{1-20}$ alkyl, Chd $3$-$20$ carbocyclic or heterocyclic groups, or pairs of substituents on the same or different amine nitrogen(s) can form one or more chains or rings, e.g., $C_{1-30}$ alkylene, $C_{3-20}$ carbocyclic or heterocyclic, cycloalkylene, arylene, aralkylene or alkarylene rings. The amine groups coordinated to the two platinum ions need not be the same. As indicated above with respect to unsymmetrical chelation of the two platinum ions by the acidic functions on the ligand, A, there may be therapeutic advantages to using different amine coordinating groups on one platinum ion from those used to coordinate the other.

Examples of suitable amine coordinate groups include, e.g., ammonia, lower alkylamines, including straight-chain and branch-chain amines, cyclic amines, e.g., pyrrolidine, piperidine, and the like; and diamines, e.g., ethylenediamine, 1,2,diaminocyclopentane and, preferably, 1,2-diaminocyclohexane. Also suitable are bidentate diamines having one amine function attached directly to an alicyclic ring, while the other is in the form of an aminomethyl substituent on the ring, e.g., 1-amino-2-aminomethylcyclohexane. This permits variation in the size of the chelate ring of bidentate amine substituents. The amine coordinating group(s) can be chiral, and the invention includes complexes made with mixtures of diastereomers, racemic mixtures and/or pure enantiomers of such chiral amines.

It will be understood that other chiral constituents, e.g., A and/or Z, of the bis-platinum complexes of the invention can also be present as mixtures of diastereomers and/or racemates or as pure enantiomers. It will sometimes be the case that a single enantiomer or racemate will have improved therapeutic properties compared to other stereoisomers.

The bis-platinum complexes of the invention are conveniently prepared by reacting potassium tetrachloroplatinite with the amine components of the eventual complex to form a diamino dichloroplatinite. Normally, this intermediate can be obtained as a precipitate from neutral aqueous solution. Advantageously, the dichloro complex is converted to the diaquo complex with silver nitrate, after which about two equivalents of the resultant diamino diaquo complex or about one equivalent of each of two diamino diaquo complexes are reacted with the ligand, A, bearing the water-solubilizing group(s), whereupon the bis-platinum complex ordinarily forms as a precipitate, which is isolated and purified by conventional procedures, e.g., filtration, washing, drying, optionally including chromatography, recrystallization and the like. The reactions are normally effected at about 0°–40° C., preferably at room temperature, under analogous conditions to those disclosed in Kidani et al.

Pt(IV) complexes are conveniently synthesized by oxidation of Pt(II) complexes, e.g., by reaction with hydrogen peroxide, normally at about 20°–80° C. It will be appreciated that, where one or both platinum ions are other than Pt(II) ions, e.g., Pt(IV) ions, additional counterions will be required to balance the charge. These counterions will generally be selected from halide, hydroxide, nitrate, azide, other pseudohalides or other organic or inorganic anions. Oxidation of Pt(II) to Pt(IV) is described in, e.g., Cotton et al, "Advanced Inorganic Chemistry", p. 854 (John Wiley, 1962).

An illustrative subclass of ligands, A, includes compounds having the formula II

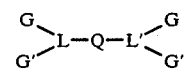

wherein LGG' and L'GG' are each independently a bidentate ligand, G and G' being said pair of platinum-coordinating acid groups (acid form); and Q is a single bond or a divalent linking group. It will be understood that the water-solubilizing function, Z, can be incorporated in any of L, L' or Q, when required.

Suitable bidentate ligands, LGG' or L'GG', include, e.g., phthalate, salicylate, catechol, ortho-hydroxysulfonate, and analogs wherein one or both G and G' functions are sulfonate or phosphonate. Fused-ring, multiple-ring, heterocyclic ring, alicyclic ring and/or non-cyclic groups bearing a pair of coordinating groups, G and G', can also be used.

Some illustrative examples of linking groups, Q, include —N=N—, —CO—, —SO$_2$—, —NHCO—(CH$_2$)$_p$—CONH— (p is an integer from 0 to 30, preferably from 2 to 8), —NHCONH—(CH$_2$)q—NHCONH— (q is an integer from 1 to 30, preferably from 1 to 8), —(CR$^1$R$^2$)$_m$—, (R$^1$ and R$^2$ are each independently H, $C_{1-20}$-alkyl, aryl, alkaryl, aralkyl, alkylidene, aralkylidene, quinoidal, and the like; m is an integer from 1 to 30), —N=N—Ar—Q'— (Ar is arylene; Q' is a divalent linking group, e.g., a single bond, —NHCO—, —NHCONH—, —CONH—, $CH_2$, —CO—, —$SO_2$— and the like), and —COO—$R^3$—OOC—($R^3$ is alkylene, arylene and the like).

Illustrative ligands of formula II include the following representative examples. The first six examples show the acid form of the ligand, the solubilizing group, Z, and also illustrate a bis-Pt complex with 1,2-diaminocyclohexane (DACH) or other amine ligand. It will be understood that other solubilizing groups and other amine ligands can be used, as set forth herein. The remaining examples show either the ligand A, alone, or A-(Z)n alone, emitting the Pt($NR^1R^2R^3$)($R^4R^5R^6$) portions of the complex.

IIA: (A-Z, Z=COOH)

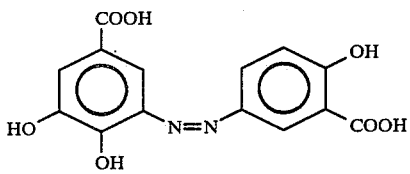

An illustrative complex of this azo-linked (Q= —N=N—) mixed catechol/salicylate ligand with (DACH) Pt(II) is:

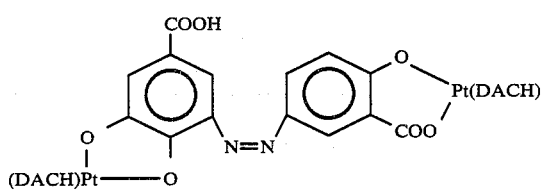

IIB: (A-Z, Z=$SO_3H$)

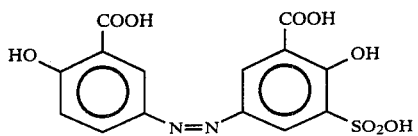

An illustrative complex of this azo-linked bis-salicylate ligand with [4-amino-5-aminomethyl-2-methylpyrimidine] Pt(II) is

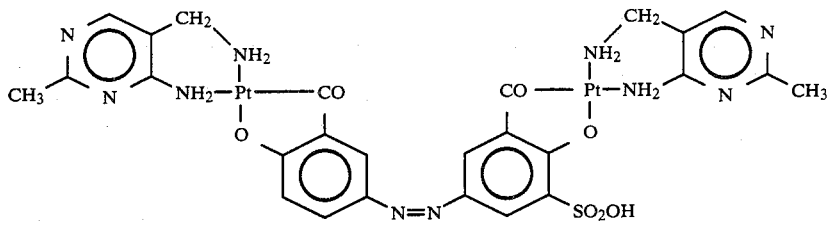

IIC: (A-$Z_2$, Z=COOH, n=2)

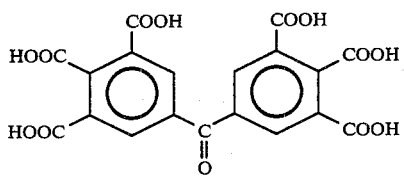

An illustrative complex of this carbonyl-linked (Q= —CO—) bis-phthalate ligand with [5,6-diaminouracil]Pt(II) is

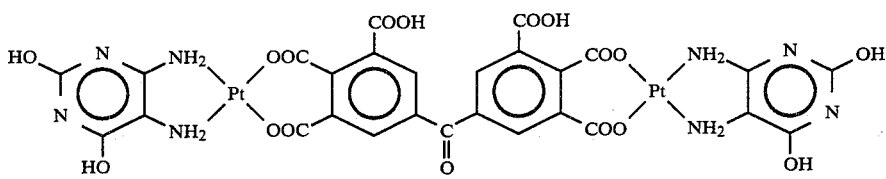

IID: (A-Z, Z=COOH)

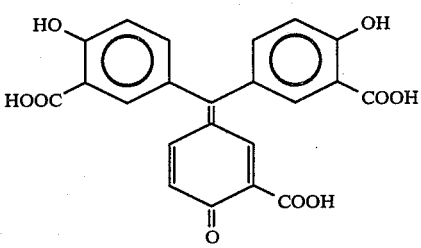

An illustrative complex of this quinoidal methylenelinded bis-salicylate ligand with (3,4-diamino-5-pyrazolol]-Pt(II) is

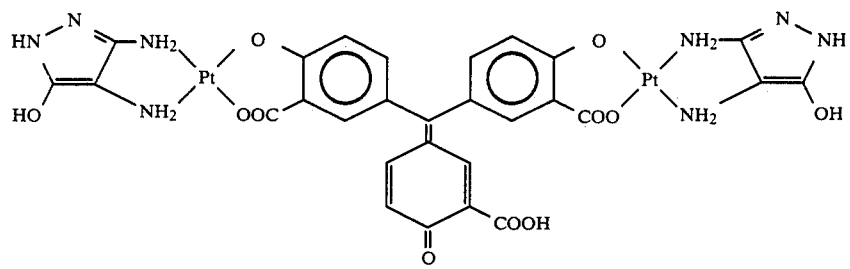

IIE: (A-Z, Z=COOH)

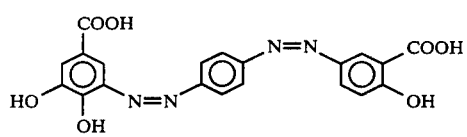

An illustrative complex of this azo-linked (Q= —N=N—Ph—N=N—) mixed catechol/salicylate ligand with [ethylenediamine]-Pt(II) is

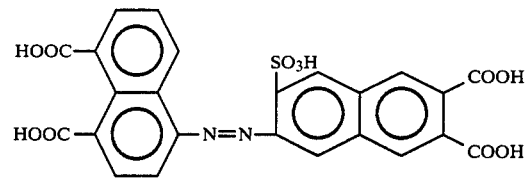

IIH: (A-Z$_2$, Z= SO$_3$H, n=2) The ligand is a hexamethylene-bis-urea-linked bis-catechol.

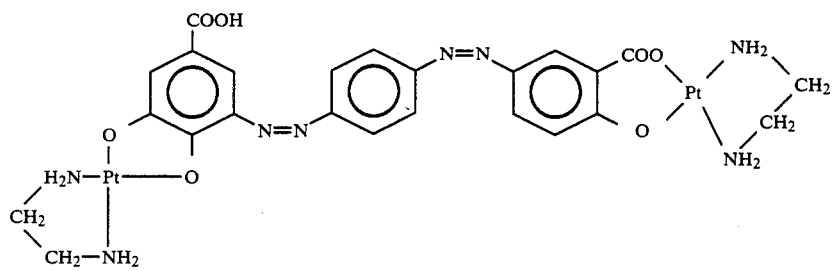

IIF: (A-Z, Z= CH$_2$COOH)

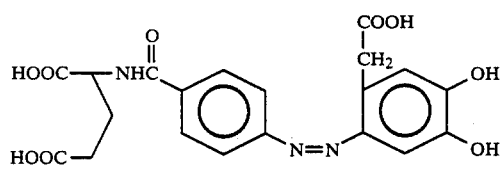

An illustrative complex of this azophenylamide-linked (Q= —NHCO—Ph—N=N—) aliphatic dicarboxylate/catechol ligand with [o-phenylenediamine]Pt(II), in which the two chelate rings to the tetradentate ligand are 8-membered and 5-membered respectively, is

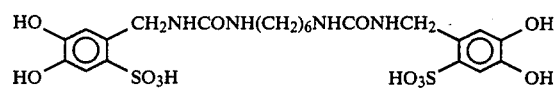

Other representative types of tetradentate ligands, A, are illustrated by the following examples. Where no solubilizing group, Z, is present, and no platinum-coordinating group is sulfonate or phosphate, at least one Pt(IV) ion will be complexed with the ligand.

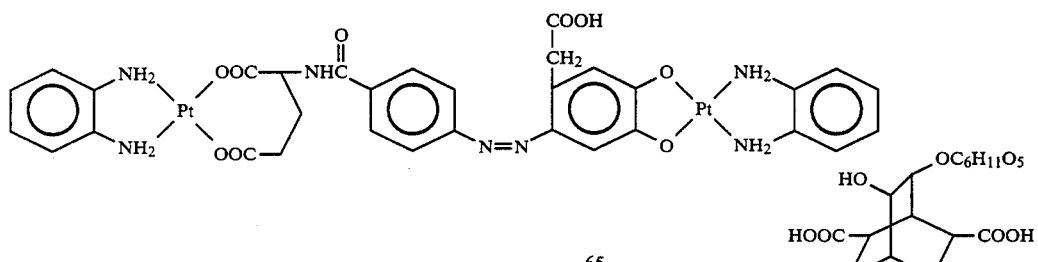

IIG: (A-Z, Z= SO$_3$H) the ligand is an azo-linked bisdicarboxylate which forms 8-membered and 7-membered Pt chelate rings.

IIIA (OC$_6$H$_{11}$O$_5$ = hexitolyl

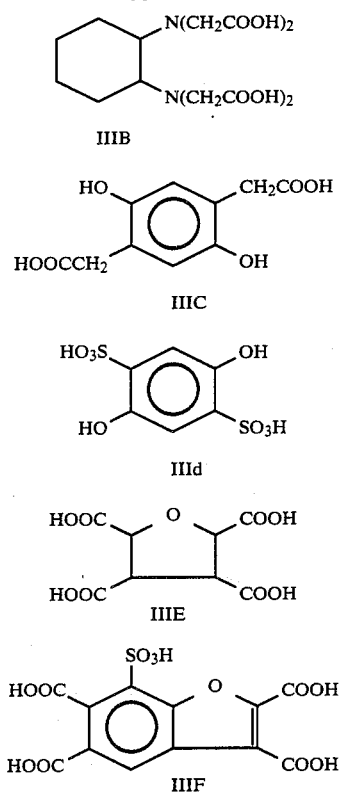

Complexes of, e.g., (DACH)Pt(II), [4-amino-5-amino-methyl-2-methylepyrimidine]Pt(II), [5,6-diaminouracil]Pt (II), [3,4-diamino-5-pyrazolol]Pt(II), [ethylenediamine]-Pt(II) and o-phenylenediamine]Pt(II) with, e.g., IIIA, IIID, IIIF, cyclopentane-1,2,3,4,5acid, 3-sulfohydroquinone-2,5-diacetic acid, pentane-1,2,3,4,5acid, 2-sulfonaphthalene-1,4,5,8-tetracarboxylic acid, bicyclo[2.2.2]-octane-2,3,5,6,7-pentacarboxylic acid, hydroquinone-2,5-diphosphonic acid, 5-hydroxy-4-phosphonyloxysalicyclic acid and butane-1,4-bis-(2-phosphonoacetic acid) are additional representative compounds according to the invention. Other representative compounds include complexes of Pt(IV) with the above diamine ligands and tetradentate ligands, and also with the tetradentate ligands IIA-H, IIIB, IIIC, IIIE, bicyclo[2.2.2]-oct-7-ene-2,3,5,6-tetracarboxylic acid, cyclobutane-1,2,3,4-tetracarboxylic acid, furan-2,3,4,5-tetracarboxylic acid, naphthalene-1,4,5,8-tetracarboxylic acid, 2,5-dihydroxyterephthalic acid, hydroquinone-2,5-diacetic acid, 2,4,5-trihydroxybenzoic acid, benzene-1,2,4,5-tetracarboxylic acid, 4-(4-salicylylazo)phthalic acid and cyclohexane-1,2,4,5-tetracarboxylic acid.

The ligand, A, bearing the water-solubilizing group(s) Z, will often be commercially available. Alternatively, this ligand can be synthesized by methods which will be apparent to the ordinary skilled art worker.

The aromatic ligands can be prepared from the unsubstituted mono- or polynuclear aromatic systems by conventional methods of aromatic substitution. Alternatively, platinum-coordinating acidic groups can be introduced by, e.g., oxidation of alkyl substituents, or a combination of acylation and oxidation to form carboxylates; sulfonation to form sulfonic acids; a combination of acylation, Baeyer-Villiger degradation and hydrolysis to form phenols; and phosphonation as described in Worms et al., "Phosphonic Acids and Derivatives", in "Organic Phosphorus Compounds", Vol. 7, pp. 1–487, Kosolapoff et al., Eds. (John Wiley, 1973), and references therein.

Alicyclic ligands can be prepared, inter alia, by catalytic hydrogenation of corresponding aromatic ligands. Other methods for synthesizing the aromatic, alicyclic and/or non-cyclic ligands bearing the platinum-coordinating acidic groups can be readily devised using conventional synthetic methods such as those in, e.g., Harrison et al., "Compendium of Organic Synthetic Methods" (Wiley-Interscience, New York, 1971); Houben-Weyl, "Die Methoden der Organischen Chemie"; Organic Syntheses (annual and collective); Theilheimer, "Synthetic Methods of Organic Chemistry"; Wagner and Zook, "Synthetic Organic Chemistry", and the like.

Entry into the subclass of compounds with ligands having the formula II, wherein Q is azo, can be conveniently gained by diazonium coupling, using conventional conditions. Many bidentate ligants, LGG', L'GG', bearing amino groups, are commercially available, and their behavior in diazonium coupling reactions is known from the dye art. Further derivatization of azo compounds, e.g., to introduce sulfonic acid solubilizing groups, is also known from this art.

Compounds of formula II, wherein Q is a bis-urea linking group, can be readily prepared by reaction of bidentate amine-substituted ligands with a polymethylenediisocyanate, under conventional conditions. Alternatively, a diester can be used as a linking reagent, to give ligands wherein Q is a bis-amide. Acylation with bis-acid halides can be used to produce bis-ketones. Sulfuryl halide sulfonation or phosgene acylation can be used to link protected bidentate ligands by sulfonyl or carbonyl groups, respectively.

Similarly, numerous amines suitable for use as amine coordinating groups will be commercially available and/or readily convertible into other groups from available starting materials, e.g., by methods such as those collected in, e.g., Harrison et al., supra, the other compendia indicated supra, and like sources.

Bidentate diamino coordinating groups, e.g., 1,2-diaminocyclohexane, can be conveniently produced from the corresponding cyclic olefin, e.g., cyclohexene, by addition across the double bond, e.g., by formation of an aziridine, followed by displacement with an amine; or by reaction of the cyclic olefin with silver cyanate and iodine, followed by displacement of the iodo group by a second amine; or by epoxidation, opening with an amine, conversion of the vicinal hydroxyl group to a leaving group, e.g., a tosylate, followed by displacement with a second amine; and similar reactions for producing vicinal substituents from olefinic starting materials. These reactions can obviously be applied to non-cyclic compounds as well.

Known compounds which can be used as the ligand, A, the complete ligand A-Z, the group, Z, or the amine $NR_1R_2 R_3$ and/or $NR_3R_5R_6$ may often be found in compilations of organic compounds, together with syntheses or isolation procedures whereby they may be produced. Such compilations include, e.g., Beilstein's "Handbuch der organischen Chemie", Elsevier's "Encyclopedia of Organic Chemistry", Heilbron's "Dictionary of Organic Compounds", Rodd's "Chemistry of Carbon Compounds", and the like. Other sources of known compounds include Chemical Abstracts, compound indices of chemical journals and computerized data bases. Even where a desired component of the complex of the invention is not known, it will generally be readily synthesized from a known precursor using methods disclosed in the aforementioned compendia or readily available to the skilled art worker The bis-platinum complexes of the invention are advantageously administered to patients, i.e., humans or animals having tumors susceptable to therapeutic treatment by platinum complexes, as sterile aqueous-solutions. The solutions are preferably administered intravenously or intraarterially, although other forms of administration may be indicated in certain cases.

Solutions for intravenous injections will normally be sterile physiological solutions, which may also contain appropriate amounts of alkali, e.g., sodium bicarbonate, to convert complexes bearing acidic water-solubilizing groups to their salts. It is also possible to use pharmaceutically acceptable surfactants, e.g., naturally occurring constituents of blood which have surface active properties, e.g., salts of bile acids such as deoxycholic acid, as dispersing and/or emulsifying agents. Such natural emulsifiers have been used to disperse antibiotics, e.g., amphotericin B, in aquequs injection media. Preferably, however, the water-soublizing group(s) will render the bis-platinum complex of the invention soluble in water without the use of such emulsifiers and/or surfactants. Suitable dosage forms can also include oily or aqueous injectable preparations, e.g., for intramuscular or intraperitoneal injection, syrups and the like liquid preparations, and solid dosage forms, e.g., capsules, tablets and the like.

The effective amounts of the complex of the invention which should be administered can be determined by conventional methods which will be apparent to the skilled clinician. Normally, the activity of the bis-platinum complex of the invention will be evaluated in a screen along with a known complex such as Cisplatin or the (DACH)Pt(II) complexes of Gale or Kidani. The relative potency and the therapeutic index, i.e., the ratio of therapeutic effectiveness to toxicity, compared to that of the known analogue will normally determine the relative dosage compared to conventional dosages of the analoque for the type of malignancy being treated. The treatment regimen can be varied in ways which are well known to the skilled clinician, as a function of the type of malignancy being treated, the condition of the patient, and the particular properties of the antitumor bis-platinum complex being administered Inevitably, a certain amount of experimentation is required to determine the optimum dosages and treatment regimens, as is normally the case for antitumor therapy. It will sometimes be advantageous to administer the bis-platinum complex of the invention in combination with one or more agents that potentiate its antitumor activity or mitigate undesired side effects. Such synergistic effects have been disclosed in, e.g., Gale et al., U.S. Pat. No. 4,137,248, where a platinum complex was administered with cyclophosphamide and 5-fluorouracil or hydroxyurea.

An antitumor effective dosage, e.g., an amount of the complex of the invention suitable for delivery of an equivalent amount of diaminoplatinum ions to the amount of such ions released by the complexes of Gale or Kidani, will generally be in the range of about 0.1–500 mg/kg/ dose.

It is recognized that certain of the bis-platinum complexes having the formula shown above will have sufficiently high toxicity and/or sufficiently low therapeutic indices as to be unsuitable for antitumor therapy. However, these parameters can be readily determined by conventional screening tests, e.g., with L-1210 murine leukemia cells implanted in mice, and such complexes can be avoided.

It should be noted that the ready solubility of the bis-platinum complexes of the invention in water is advantageous for oral administration. Depending on the stability, the potency, the bioavailability and the side effects of a particular compound, oral administration may be indicated.

Without being bound by any mechanism or theory, it is nevertheless considered likely that cis-diaminoplatinum complexes are fully or partially hydrolysed in the blood stream, in the tissues or even in solution, to generate the (diamine)Pt(II) or (diamine)Pt(IV) moiety having water or chlorine in some or all of the remaining coordination sites. The bis-platinum complexes of the invention have the advantage of being able to deliver two identical or different diaminoplatinum ions by sequential hydrolysis of the two pairs of platinum-coordinating groups from a symmetrical or unsymmetrical tetradentate carrier ligand, A, while at the same time being able to carry two diaminoplatinum moieties in a single soluble complex.

As noted above, prior art platinum antitumor complexes generally have had a single Pt ion. The advantages of the bis-platinum complexes of the invention include the possibility of tailoring the complex to deliver two sequential doses of diaminoplatinum ions at a chosen rate and with a theapeutically beneficial time delay. This could permit both quantitatively and qualitatively improved delivery of antitumor diaminoplatinum ions to tumor sites.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of benzenepentacarboxylatobis [(1,2-diaminocyclohexane) platinum(II)]

An 8 gram portion of platinum metal was digested in 250 ml of aqua regia to form chloroplatinic acid. Potassium chloride (12 g) solution was added to immediately precipitate potassium hexachloroplatinate(IV) which was subsequently reduced to potassium tetrachloroplatinite (II) with 2 grams of hydrazine hydrochloride. To the red aqueous solution of potassium tetrachloroplatinite was added 6 ml of 1,2-diaminocyclohexane (Aldrich) and enough 0.5N NaOH to adjust the pH to 7. After overnight stirring, 10 grams (64% yield) of dichloro(1,2-diaminocyclohexane)platinum was collected as a yellow precipitate. The commercial diaminocyclohexane used in this synthesis was a mixture of cis and trans isomers and the platinum complex was therefore also an isomeric mixture. It should be noted that isomerically pure complex can be prepared from readily synthesized cis and trans isomers of diaminocyclohexane or from easily resolved pure enantiomers thereof, as prepared by the process of, e.g., U.S. Pat. No. 4,169,846.

Dichloro(1,2-diaminocyclohexane)platinum (10 g; 26.3 mmole) and silver nitrate (8.5 g; 521 mmole) were reacted in 100 ml of deionized water overnight at room temperature, protected from light. The insoluble silver chloride was filtered off on a glass frit and 3.6 g (12.1 mmole) of benzenepentacarboxylic acid (Pfalz 8 Bauer) dissolved in 100 ml of water was added to the filtrate and the pH of the solution was adjusted to 5 with sodium hydroxide. The mixture was allowed to stand at 40° for 2 hours and the yellow-white precipitate was collected and washed with water, ethanol, and ether and dried in vacuo to yield 6.2g (52%) of benzenepentacarboxylatobis[(1,2-diaminocyclohexane)platinum(II) tetrahydrate]. Elemental analysis for $C_{23}H_{30}N_4O_{10}Pt_2 \cdot 4H_2O$: Calculated C, 28.05; H, 3.89; N, 5.68; Found C, 27.89; H, 3.91; N, 5.64.

The infrared spectrum as a KBr pellet shows a major peak at 1600 cm$^{-1}$, indicative of platinum-bound carboxyl groups and a small peak at 1700 cm$^{-1}$, indicative of a free carboxyl group. The compound is insoluble in water and common organic solvents, but dissolves readily in 1% NaHCO$_3$. Thin layer chromatography of a bicarbonate solution of the compound on reverse phase silica gel plates eluted with methanol/water (2/1) gives a SnCl$_2$ positive spot at R$_f$=0.85.

EXAMPLE 2

Antitumor activity of benzenepentacarboxylatobis-[(1,2-diamonocyclohexane) platinum(II)]

The bis-platinum complex of Example 1, dissolved in 1% NaHCO$_3$ solution, was screened against the murine tumor line L1210 leukemia over a dose range of 2.5–20 mg/kg and a dose schedule of daily×7 and days 1, 5, and 9. The results are presented in Table I. A dose of 20 mg/kg was toxic on the daily×7 schedule and 40 mg/kg was toxic on the days 1, 5, 9 schedule.

TABLE I

| Dose (mg/kg) | Percent Increase in Lifespan[a] | |
|---|---|---|
| | Daily × 7 | Drugs 1, 5 and 9 |
| 2.5 | 87 | 21 |
| 5.0 | 117 | 43 |
| 10.0 | 61 | 135 |
| 20.0 | — | 193 |

[a]Treatment uas started 24 hours after inoculation of × 10$^6$ L1210 cells in a CDF$_1$ mic. The drug was administered intraperitoneally.

[a]Treatment was started 24 hours after inoculation of 1 × 10$^6$ L1210 cells in CDF$_1$ mice. The drug was administered intraperitoneally.

The test showed this compound to be active against the experimental murine tumor line L1210 leukemia. Its solubility of greater than 10 mg/ml in 1% NaHCO$_3$ solution allows it to be readily administered to patients.

EXAMPLE 3

Preparation of hydroquinone-2,5-disulfonato bis[(1,2-diaminocyclohexane) platinum(II)]

To an aqueous solution of dinitrato (1,2-diaminocyclohexane) platinum(II), prepared according to Example 1, was added ½ equivalent of a solution of hydroquinone-2,5-disulfonic acid dipotassium salt (Aldrich), to which an equivalent of potassium hydroxide was added to form the tetrapotassium salt. An immediate white precipitate formed which was collected, washed thoroughly with water and dried in vacuo. 0.9 grams of the sulfonic acid (2.6 meq) yielded 1.2 grams of the bis-platinum complex (56%). An infrared spectrum of the product had strong absorptions at 3200, 2920, 2830, 1590, 1410, 1170, 1160, 1060, 1010, 800 and 650 cm$^{-1}$.

The product dissolved in 1% NaHCO$_3$ solution.

By an analogous procedure, the hydroquinone-2,5-disulfonate bis-Pt(II) complexes of: [4-amino-5-aminomethyl-2-methylpyrimidine]Pt(II), [5,6-diaminouracil]Pt(II), [3,4-diamino-5-pyrazolol]Pt(II), [ethylenediamine]Pt(II) and [o-phenylenediamine]Pt(II) are prepared.

EXAMPLE 4

Preparation of benzenepentacarboxylatcbis[ethylenediamine]platinum-(II)]

Dichloro (ethylenediamine) platinum(II) was prepared from the reaction of potassium tetrachloroplatinate and ethylenediamine. The reactants were stirred in water at room temperature to give a yellow precipitate which was collected, washed with water and dried in vacuo over calcium chloride overnight. The product was then reacted with 1.9 equivalents of silver nitrate dissolved in water and the mixture was stirred for 12 hours, protected from light. Silver chloride was removed by filtration.

To the filtrate was added ½ equivalent of benzenepentacarboxylic acid dissolved in water. The pH of the solution was adjusted to 4.5 with 1N NaOH solution. The solution was warmed at 40° C. for 1 hour and a tan precipitate formed, which was collected, washed and dried. In one preparation, 200 mg of benzenepentacarboxylic acid (0.67 meq) yielded 250 mg of product.

An infrared spectrum of the product had absorptions at 3200, 3100, 1700(sh), 1600, 1320, 1140, 1050 cm$^{-1}$. The shoulder at 1700 indicates unbound carboxyl group, while a stronger absorption at 1600 cm$^{-1}$ shows platinux-bound carboxylate groups.

The product dissolves in 1% NaHCO$_3$ solution.

By an analogous procedure, [ethylenediamine]Pt(II) complexes of IIA-H are prepared.

EXAMPLE 5

Preparation of aurintricarboxylatobis[(1,2-diaminocyclohexane) platinum(II)]

To 120 mg of aurintricarboxylic acid (0.28 meq) (Aldrich) was added 1 ml of 1N NaOH to form a solution at pH=12. To this solution was added an aqueous solution of dinitrato (1,2-diaminocyclohexane) platinum (250 mg; 0.57 meq), prepared according to Example 1, and the pH was reduced to 5.7. An immediate red precipitate formed. After drying, 250 mgs (85% yield) was collected. An infrared spectrum of the product showed peaks at 3200, 3100, 2920, 2840, 1600(sh), 1560, 1360, 800 cm$^{-1}$.

By an analogous procedure, the aurintricarboxylato complexes of [4-amino-5-aminomethyl-2-methylpyrimidine]Pt(II), [5,6-diaminouracil]Pt(II), [3,4-diamino-5-pyrazolol]Pt(II), [ethylenediamine]Pt(II) and [o-phenylenediamine]Pt(II) are prepared.

EXAMPLE 6

Preparation of 5,5'-carbonylbistrimellito bis
[(1,2-diaminocyclohexane)platinum(II)]

5,5'-Carbonylbistrimellitic acid (223 mg; 0.5 meq) (Aldrich) was dissolved in water with the addition of 2 ml of 1N NaOH. Dinitrato (1,2-diaminocyclohexane) platinum (500 mg; 1.1 meq) was added and the pH of the resulting mixture was maintained at 5. The mixture was kept at room temperature and after 30 minutes a white precipitate started to form. The product was collected by filtration, washed with water and dried in vacuo to yield 350 mg (63%) of product.

The product dissolves readily in 1% $NaHCO_3$ solution. An infrared spectrum of the product had the following peaks: 3200, 3100, 2920, 2840, 1780(C=O), 1700(sh), 1580, 1380, 960, 800, 690 $cm^{-1}$.

By an analogous procedure, the 5,5-carbonylbis-trimellito complexes of
[4-amino-5-aminomethyl-2-methylpyrimidine]Pt(II), [5,6-diaminouracil]Pt(II), [3,4-diamino-5-pyrazolol]Pt(II), [ethylenediamine]Pt(II), and [o-phenylenediamine]Pt(II) are prepared.

EXAMPLE 7

Preparation of 5-(2-carboxy-4,5-dihydroxyphenylazo) salicylatobis[(1,2-diaminocyclohexane)platinum(II)]

0.005 Mole of 5-aminosalicylic acid, in 35 ml of 0.5M HCl was cooled to 0° C., and treated with 0.0052 mole $NaNO_2$ in 2 ml deionized water to form the diazonium salt. A suspension of the diazonium salt was transferred to an addition funnel and added over 70 minutes to an ice cooled solution of 3,4-dihydrozybenzoic acid (0.005 mole) in 47 ml of 0.5M aqueous $NaHCO_3$ with stirring, to produce a dark red product. The reaction mixture was diluted with 120 ml of cold water, and 14.5 ml of 1M HCl was added, resulting in separation of solid product, which was filtered and vacuum dried.

The azo-coupled catechol/salicylate was dissolved in water with 2 equivalents of base, and reacted with 2 equivalents of dinitrato(1,2-diaminocyclohexane) platinum(II), as in the procedure of Example 1, except that the pH was adjusted to 9.3 with 1N NaOH. A reddish-brown precipitate formed (60% yield), which was very soluble in 1% $NaHCO_3$ solution.

The infrared spectrum had peaks at 3200, 3100, 2900, 2850, 1700, 1600, 1480, 1440(azo), 1380, 790 $cm^{-1}$.

By an analogous procedure, the azo-linked complexes mentioned above can be prepared.

EXAMPLE 8

Preparation of hydroquinone-2,5-diacetato bis[(1,2-diaminocyclohexane)platinum(IV)]

2,5-Hydroquinone-2,5-diacetic acid (125 mg; 0.55 meg) (Aldrich) was dissolved in water with the addition of NaOH. Dinitrato (1,2-diaminocyclohexane) platinum (500 mg; 1.15 meg) was added, and the pH of the resulting solution was adjusted to 7. After 1 hour at room temperature, a tan precipitate formed. The product, hydroquinone-2,5-diacetato bis[(1,2-diaminocyclohexane) platinum (II)] was collected, washed with water and dried to yield 200 mg (43%). The infrared spectrum of the product had peaks at 3200, 3100, 2920, 2840, 1560, 1360, 1200, 1050, 1020 $cm^{-1}$.

The compound is insoluble in basic solutions.

The compound was then suspended in water at 60° and 3 ml of 30% hydrogen peroxide was added dropwise to form a yellow solution. Unreacted starting material was filtered off and the filtrate was evaporated to 10% volume. Ethanol was then added to precipitate a yellow product. The infrared spectrum of this platinum (IV) compound had the following peaks: 3200, 3100, 2920, 2840, 1700, 1600, 1360, 690, 560 $cm^{-1}$.

By an analogous procedure, Pt (IV) complexes corresponding to each of the Pt (II) complexes mentioned above can be prepared, as can Pt (IV) complexes of the tetradentate ligands IIA-H, IIIB, IIIC, IIIE, bicyclo[2.2.2]oct-7-ene-2,3,5,6-tetracarboxylic acid, cyclobutane-1,2,3,4-tetracarboxylic acid, furan-2,3,4,5-tetracarboxylic acid, naphthalene-1,4,5,8-tetracarboxylic acid, 2,5-dihydroxyterephthalic acid, hydroquinone-2,5-diacetic acid, 2,4,5-trihydroxybenzoic acid, benzene-1,2,4,5-tetracarboxylic acid, 4-(4'-salicylylazo)phthalic acid, and cyclohexane-1,2,4,5-tetracarboxylic acid.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

We claim:

1. A bis-platinum complex having the formula

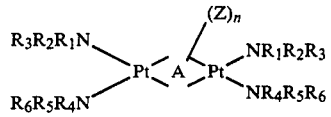

wherein A is a ligand having two pairs of platinum-coordinating acidic groups which are each independently a carboxylate, phenolate, sulfonate or phosphonate group, each said pair being capable of coordinating with a platinum ion to form a 5–10 membered chelate ring; Z is a water-solubilizing group; n is 0 or a positive integer, with the proviso that n is 0 only when at least one of said platinum-coordinating acidic groups is sulfonate or phosphonate, or when at least one platinum ion is a Pt(IV) ion; and $R_1$, $R_2$, $R_3$, $R_4$, $R_5$ and $R_6$ are each independently H or a $C_{1-20}$ alkyl, aryl, aralkyl or alkaryl group, or together form one or more $C_{1-30}$ alkylene, cycloalkylene, arylene, aralkylene or alkarylene groups; or a pharmaceutically acceptable salt thereof.

2. A complex according to claim 1, wherein A is a mononuclear, dinuclear or trinuclear aromatic ring system.

3. A complex according to claim 2, wherein said aromatic ring system is a benzene or naphthalene ring.

4. A complex according to claim 3, wherein $R_1$ and $R_4$ together are 1,2-cyclohexylene, and $R_2$, $R_3$, $R_5$ and $R_6$ are each H.

5. Benzenepentacarboxylatobis[(1,2-diaminocyclohexane)platinum(II)], a complex according to claim 4.

6. A complex according to clai 3, wherein A is

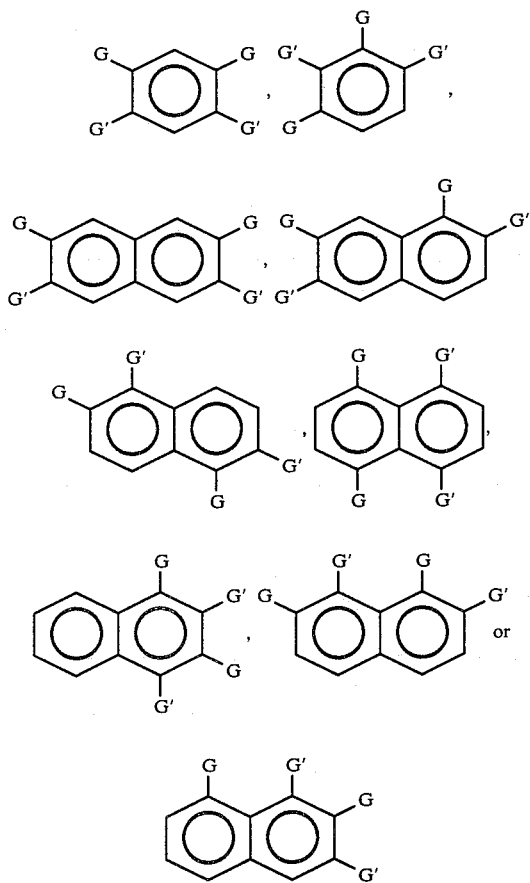

wherein G and G' are said pair of platinum-coordinating acid groups.

7. A complex according to claim 6, wherein G and G' are both carboxylate groups

8. A complex according to claim 6, wherein at least one G is a phenolate oxygen.

9. A complex according to claim 6, wherein in each said G and G' pair, one of G and G' is a carboxylate group and the other is a phenolate oxygen.

10. A complex according to claim 1, wherein A is a monocyclic or polycyclic alicyclic ring system.

11. A complex according to claim 1, wherein A is a non-cyclic aliphatic chain.

12. A complex according to claim 1, wherein $R_1$ and $R_4$ together are 1,2-cyclohexylene; and $R_2$, $R_3$, $R_5$ and $R_6$ are each H.

13. A complex according to claim 1, wherein Z is COOH or $SO_3H$.

14. A complex according to claim 1, wherein Z is a $C_{1-12}$ polyhydroxylic group.

15. A complex according to claim 14, wherein Z is a mono- or polysaccharide moiety 16. A complex according to claim 1, wherein Pt is Pt(II).

17. A complex according to claim 1, wherein n is 1–4.

18. A complex according to claim 1, wherein A has the formula

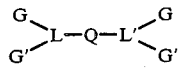

wherein LGG' and L'GG' are each independently a bidentate ligand, G and G' being said pair of platinum-coordinating acid groups; and Q is a divalent linking moiety.

19. A complex according to claim 18, wherein Q is —N=N—; —CO—; —SO$_2$—; —NHCO—(CH$_2$)$_p$—CONH—, p being an integer from 0 to 30; —NHCONH—(CH$_2$)$_q$—NHCONH—, q being an integer from 1 to 30; —(CR$^{1 l}$R$^2$)m—, R$^1$ and R$^2$ each independently being H, C$_{1-20}$-alkyl, aryl, alkaryl, aralkyl, alkylidene, aralkylidene or quinoidal, m being an integer from 1 to 30; —N=N—Ar—Q'—, Ar being arylene; Q' being a divalent linking group selected from a single bond, —NHCO—, —NHCONH—, —CONH—, CH$_2$, —CO— and —SO$_2$—; and —COO—R$^3$—OOC—, R$^3$ being alkylene or arylene.

20. A complex according to claim 18, wherein L and L' are each aryl; and Q is —N=N— or —CO—.

* * * * *